(12) United States Patent
Lee et al.

(10) Patent No.: US 8,198,462 B2
(45) Date of Patent: Jun. 12, 2012

(54) DENDRITIC PHOTOACTIVE COMPOUND COMPRISING OXIME ESTER AND METHOD FOR PREPARING THE SAME

(75) Inventors: Keon-Woo Lee, Namyangju-si (KR); Chang-Ho Cho, Anseong-si (KR); Kyoung-Hoon Min, Asan-si (KR); Raisa Kharbash, Daejeon (KR); Chang-Soon Lee, Daejeon (KR); Sung-Hyun Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 142 days.

(21) Appl. No.: 12/452,690

(22) PCT Filed: Jul. 15, 2008

(86) PCT No.: PCT/KR2008/004154
§ 371 (c)(1),
(2), (4) Date: Jan. 15, 2010

(87) PCT Pub. No.: WO2009/011538
PCT Pub. Date: Jan. 22, 2009

(65) Prior Publication Data
US 2010/0145068 A1  Jun. 10, 2010

(30) Foreign Application Priority Data
Jul. 18, 2007  (KR) .................. 10-2007-0071545

(51) Int. Cl.
*C07D 209/82* (2006.01)
(52) U.S. Cl. .................. 548/444; 548/427; 548/440
(58) Field of Classification Search .................. 548/427, 548/440, 444
See application file for complete search history.

(56) References Cited

U.S. PATENT DOCUMENTS

| | | | |
|---|---|---|---|
| 4,202,697 A | 5/1980 | Van Goethem et al. | |
| 4,255,513 A | 3/1981 | Laridon et al. | |
| 4,590,145 A | 5/1986 | Itoh et al. | |
| 5,776,996 A | 7/1998 | Okamoto et al. | |
| 6,001,517 A | 12/1999 | Kawamonzen | |
| 6,051,367 A | 4/2000 | Kunita et al. | |
| 6,596,445 B1 | 7/2003 | Matsumoto et al. | |
| 2010/0136467 A1 | 6/2010 | Matsumoto et al. | |

FOREIGN PATENT DOCUMENTS

| | | |
|---|---|---|
| DE | 199 28 742 | 12/1999 |
| JP | 61-118423 | 6/1986 |
| JP | 64-068750 | 3/1989 |
| JP | 3-004226 | 1/1991 |
| KR | 10-2010-0017754 | 2/2010 |
| WO | WO 00/52530 | 9/2000 |
| WO | WO 02/100903 | 12/2002 |
| WO | WO 2005/080337 | 9/2005 |
| WO | WO 2006/043638 | 4/2006 |
| WO | WO 2008/138732 | 11/2008 |

OTHER PUBLICATIONS

Mizukami et al (2005): STN International HCAPLUS database, Columbus (OH), accession No. 2005: 962213.*
Ingwall et al., "Hologram recording with a new photopolymer system", Optical Engineering, vol. 24, No. 5, 1985, pp. 808-811.
Kirsch et al., "Design of photopolymer holograms for optical interconnect applications", Optical Engineering, vol. 27, No. 4, 1988, pp. 301-308.

* cited by examiner

*Primary Examiner* — Golam M M Shameem
(74) *Attorney, Agent, or Firm* — McKenna Long & Aldridge LLP

(57) ABSTRACT

The present invention relates to a dendritic photoactive compound that comprises oxime ester and a method for producing the same. Since the compound according to the present invention comprises two or more oxime ester groups and chromophores in one molecule at the same time, the solubility in respects to the organic solvent and the efficiency for producing a radical by absorbing ultraviolet rays are excellent. In addition, it can act as an effective initiator in respects to the photopolymerization of the unsaturated group, in particular, the acryl compound.

10 Claims, 2 Drawing Sheets

[Fig. 1]
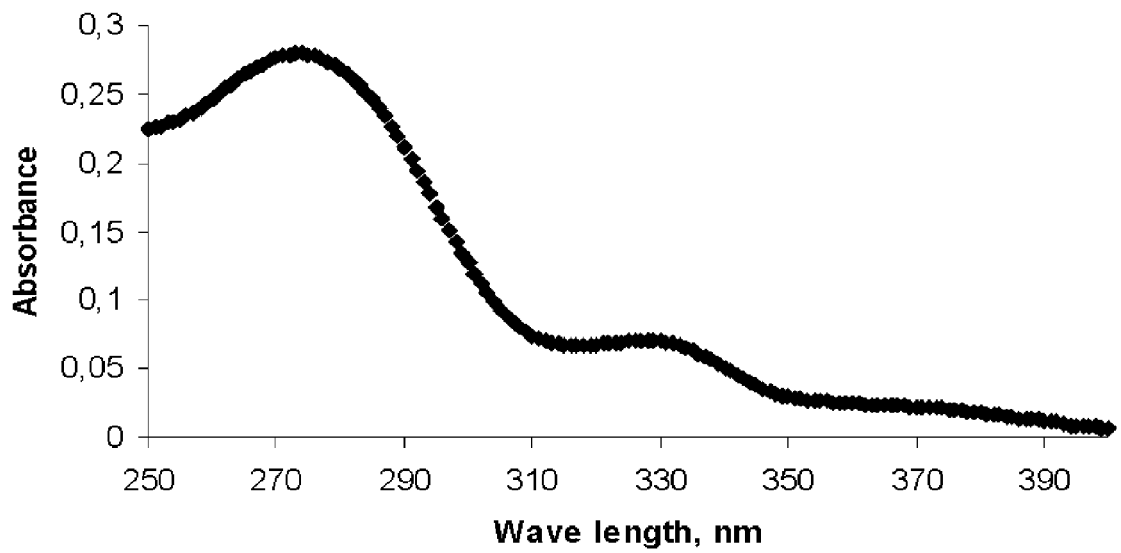
[Fig. 2]
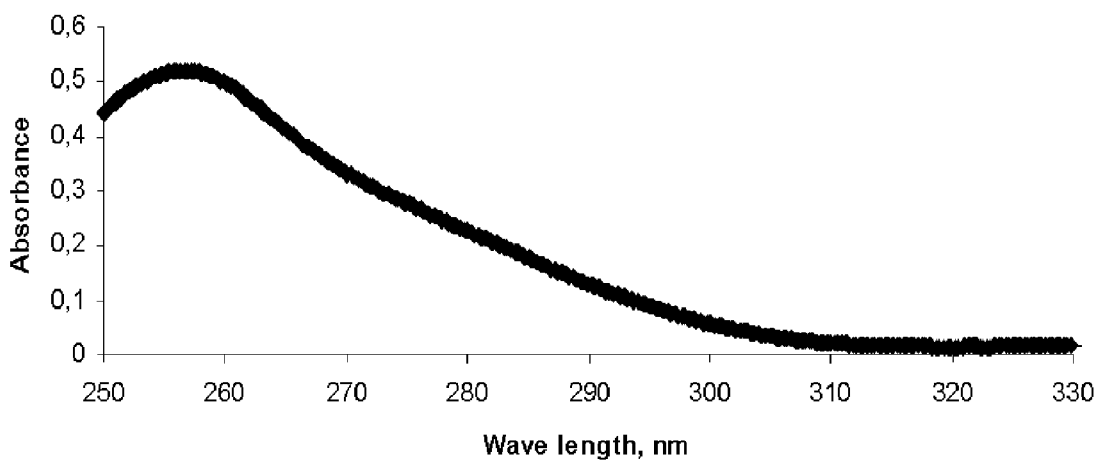
[Fig. 3]
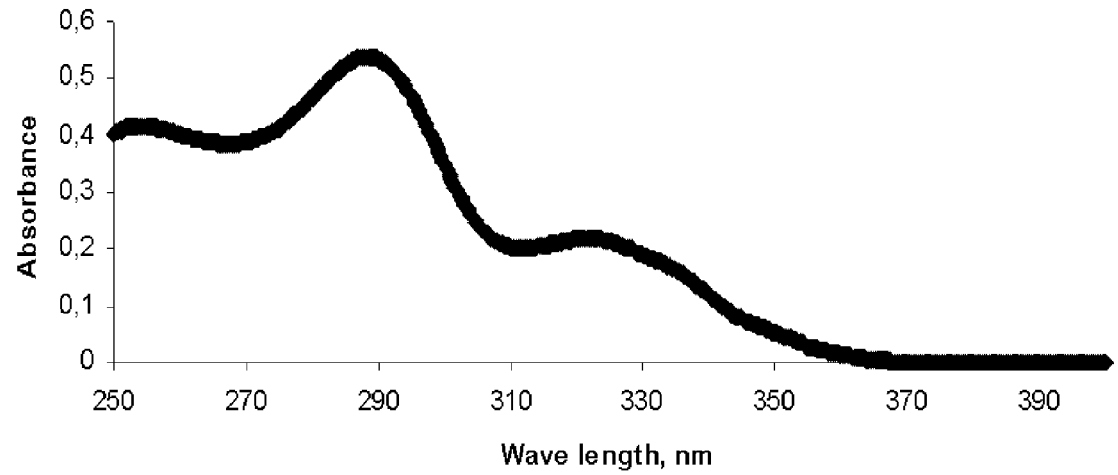

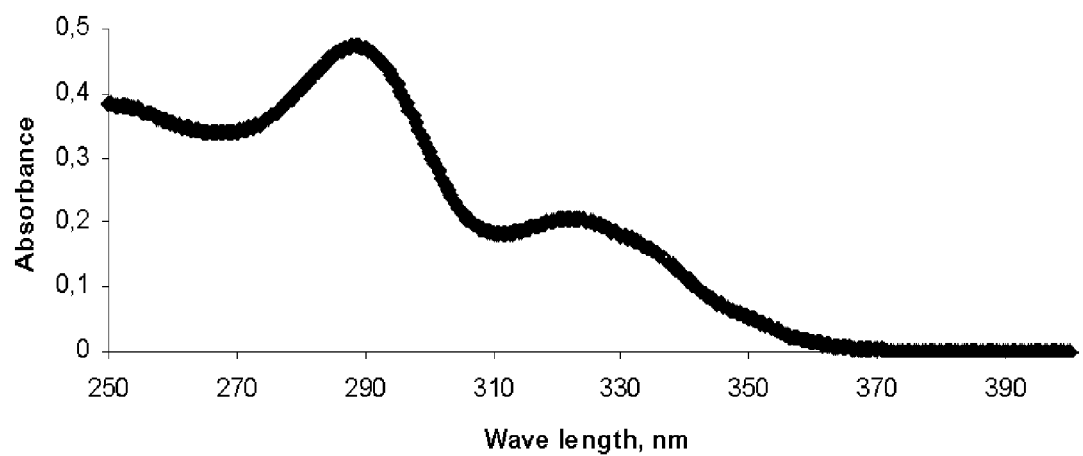
[Fig. 4]
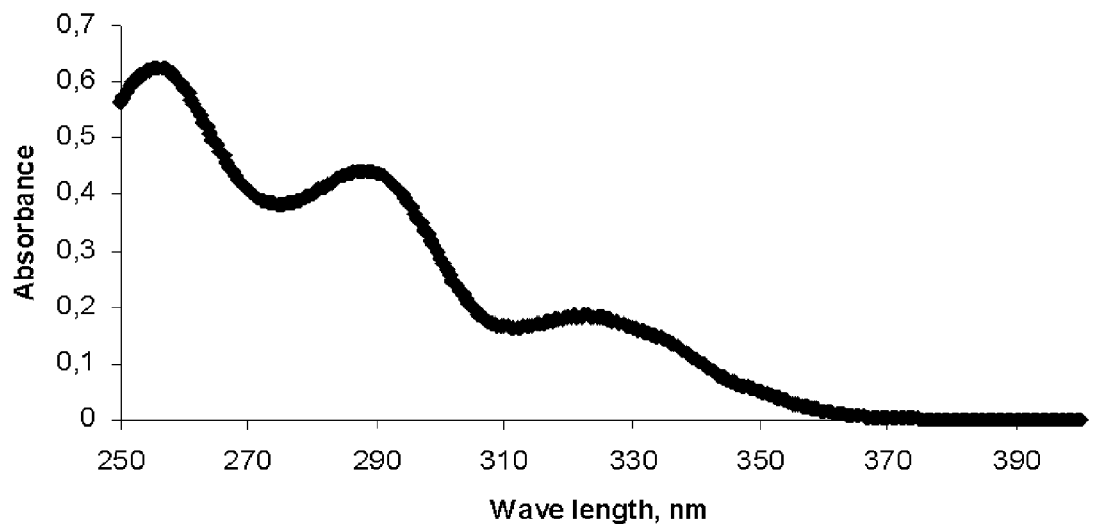
[Fig. 5]

US 8,198,462 B2

DENDRITIC PHOTOACTIVE COMPOUND COMPRISING OXIME ESTER AND METHOD FOR PREPARING THE SAME

TECHNICAL FIELD

The present invention relates to a dendritic photoactive compound that comprises oxime ester and a method for producing the same.

This application claims priority benefits from PCT/KR2008/004154, filed on Jul. 15, 2008 and Korean Patent Application No. 10-2007-0071545, filed on Jul. 18, 2007, the entire content of which is fully incorporated herein by reference.

BACKGROUND ART

The photoactive compound is a material that producing the atom or molecule which chemically carries activity by absorbing light to be decomposed, and is widely used as the photosensitive composition. As examples of the material carrying the chemical activity, there are the acid or the base, the radical and the like. In particular, the photoactive compound that produces the radical may be used in conjunction with an acryl group that causes the polymerization reaction in conjunction with the radical and may be used for the purpose of improving the strength of the coated film. As the photosensitive composition for this purpose, there is ink for inkjet or a transparent or colored protection film such as automobiles, mobile phones or the like. In addition, according to the polymerization reaction by light, it is applied to the photosensitive resin composition for the optical etching method using a phenomenon in which the solubility is reduced. As a representative example thereof, there are photopolymerization types of photosensitive composition that is used to produce a color filter of a liquid crystal display device or a photosensitive composition for a resin black matrix.

In general, the photosensitive composition comprises a polymer resin compound, a polymerizable compound that comprises an ethylenically unsaturated bond, a solvent, and a photoactive compound.

As a general example of the photoactive compound that is used in the photosensitive composition, various types of derivatives such as a acetophenone derivative, a benzophenone derivative, a biimidazole derivative, an acylphosphine oxide derivative, a triazine derivative, an oxime ester derivative and the like are known. Among them, in the case of the oxime ester derivative, since it absorbs the ultraviolet rays, it hardly shows the color, there are advantages in that the efficiency of the radical generation is high, and the stability in the composition is excellent.

Japanese Unexamined Patent Application Publication Nos. 61-118423, 1-68750, and 3-4226 disclose the use of the α-oxo oxime derivative as a photoresist photoinitiator for photoimaging and print wiring plates, and a document (Opt. Eng. 24 (1985) 808; J. Opt. Eng. 27 (1988) 301) discloses the use of the α-oxo oxime derivative as a holography photoinitiator.

In particular, in respects to the photoinitiator of the oxime ester structure, U.S. Pat. No. 4,590,145 discloses a photoinitiation system using thiooxanthone and the oxime ester compound, and U.S. Pat. No. 4,255,513 discloses an oxime ester photoinitiation system using p-dialkylaminobenzene as a synergist.

U.S. Pat. No. 5,776,996 discloses a photoinitiator using a photopromoting pigment, a titanocene compound, and β-aminooxime, and U.S. Pat. No. 6,051,367 discloses an oxime ether photoinitiator in which an ethylenically unsaturated group capable of participating in the photopolymerization is comprised in a molecule structure. WIPO 00/52530 and Germany Unexamined Patent Application Publication No. 199 28 742 A1 disclose oxime ether, oxime ester, in particular, a photosensitive composition using oxime sulfonate as a photoinitiator.

WIPO 02/100903 A1 discloses an oxime ester compound having the structure combined with alkyl acyl ketone, diaryl ketone or ketocumarine.

In addition to these, in respects to the oxime ester structure, U.S. Pat. No. 4,202,697 discloses that it is used as the etch resist, and U.S. Pat. No. 6,001,517 discloses that it is used as a photosensitive thermosetting accelerator in a posi-type photosensitive composition.

However, in the used oxime derivative compound, the compound that was developed at an early step has the low photoinitiation efficiency, and in the case of when the color property is excellent, it is not effective to absorb the UV light source. In the compounds that are announced after 1990's latter half, the photoinitiation efficiency is very improved, but they cannot sufficiently satisfy the reduced process time that is currently enhanced. In particular, since the concentration of the pigment is high or the thick film that has the thickness of the coating film of 2.5 μm or more is not sufficiently cured, it is difficult to form a fine pattern, and the formed pattern cannot show the required size and the mechanical strength. In addition, since a difference between solubilities in respects to various solvents is large, there are many cases of when its use is limited.

Therefore, the development for a photoactive compound that is capable of improving the solubility in respects to an organic solvent, efficiently absorbing ultraviolet rays, and improving the reactivity in respects to light, that is, the sensitivity is required.

DISCLOSURE OF INVENTION

Technical Problem

The present inventors have synthesized a photoactive compound that is excellent in solubility and sensitivity in respects to the organic solvent by including two or more oxime esters and having the dendritic structure, compared the solubility and the sensitivity of this compound to the solubility and the sensitivity of a known compound that comprises oxime ester, and found that its properties are excellent.

Therefore, it is an object of the present invention to provide a dendritic photoactive compound that comprises oxime ester which is excellent in solubility in respects to the organic solvent and good in sensitivity. In addition, it is another object of the present invention to provide a method for producing a dendritic photoactive compound that comprises oxime ester.

Technical Solution

The present invention provides a dendritic photoactive compound that comprises oxime ester.

In addition, the present invention provides a method for producing a dendritic photoactive compound that comprises oxime ester.

Advantageous Effects

Since the compound according to the present invention comprises two or more ester groups and chromophores in one molecule at the same time, the solubility in respects to the organic solvent and the efficiency for producing a radical by absorbing ultraviolet rays is excellent. In addition, it can act as an effective initiator in respects to the photopolymerization of the unsaturated group, in particular, the acryl compound.

BRIEF DESCRIPTION OF THE DRAWINGS

FIG. 1 is a UV spectrum that is measured after a substance of Formula 4 is dissolved in acetonitrle in the concentration of $10^{-5}$ M;

FIG. 2 is a UV spectrum that is measured after a substance of Formula 7 is dissolved in chloroform in the concentration of $10^{-5}$ M;

FIG. 3 is a UV spectrum that is measured after a substance of Formula 10 is dissolved in chloroform in the concentration of $10^{-5}$ M;

FIG. 4 is a UV spectrum that is measured after a substance of Formula 14 is dissolved in chloroform in the concentration of $10^{-5}$ M; and FIG. 5 is a UV spectrum that is measured after a substance of Formula 17 is dissolved in chloroform in the concentration of $10^{-5}$ M.

BEST MODE FOR CARRYING OUT THE INVENTION

The present invention provides a dendritic photoactive compound that comprises oxime ester that is represented by the following Formula 1a or Formula 1b.

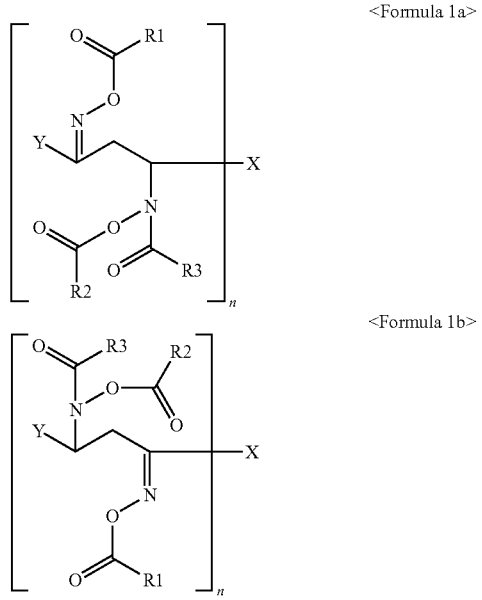

<Formula 1a>

<Formula 1b>

In the Formula 1a and Formula 1b,
n is 2,
X is a $C_2$~$C_6$ alkylene group; phenylene, biphenylene, bisphenylene, styrylene, or naphthylene that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; a $C_5$~$C_{20}$ arylene group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; or a $C_4$~$C_{20}$ divalent heterocyclic group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group and comprises O, N or S; or is selected from the group consisting of the following Structural Formulae (* is a connection portion),

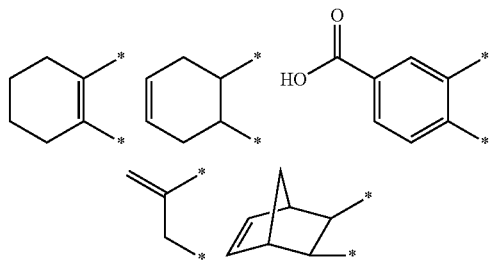

Y is selected from the group consisting of a $C_1$~$C_6$ alkyl group; a phenyl group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; a $C_5$~$C_{20}$ aryl group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; and a $C_4$~$C_{20}$ heterocyclic group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group and comprises O, N or S, and R1, R2, and R3 are each independently selected from the group consisting of a $C_1$~$C_6$ alkyl group, nitrile group and phenyl group.

It is preferable that X is an aromatic structure that is capable of absorbing light at a range of ultraviolet rays, in particular, a range of 250~450 nm, and it is not particularly limited as long as it is a functional group that performs this function, but it is preferable to use the compound that has the following Structural Formulae.

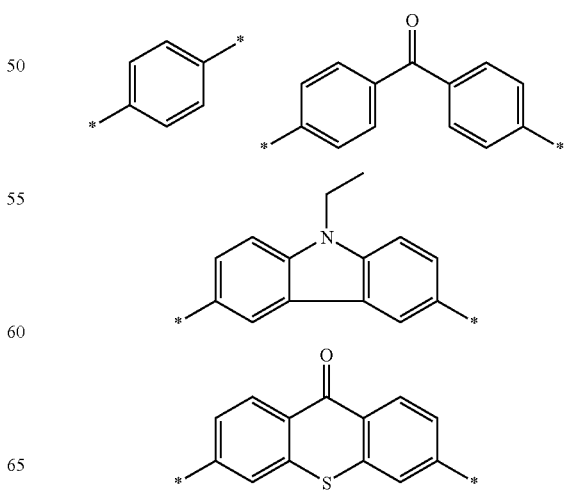

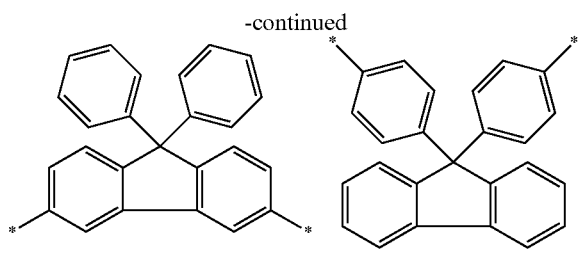

In the structure, since R1~R3 are portions in which molecules of Formula 1a or Formula 1b absorb light and then decomposed to form radicals, it is better as its mass is reduced, and it is not particularly limited to the structure.

In addition, the present invention provides a method for producing a dendritic photoactive compound that is represented by Formula 1a or Formula 1b and comprises oxime ester.

The method for producing a dendritic photoactive compound according to the present invention comprises the steps of 1) reacting ketone that is substituted with aldehyde and methyl under the presence of the base to produce the compound that is represented by the following Formula 1c or Formula 1d;

2) adding $NH_2OH \cdot HCl$ and a sodium salt of a carboxylic acid to the compound that is produced in the step 1) to produce the compound that is represented by the following Formula 1e or Formula 1f; and 3) adding R1—C(O)—Cl, R2—C(O)—Cl, R3—C(O)—Cl and the base to the compound that is produced in the step 2) to produce produce the compound that is represented by the Formula 1a or Formula 1b.

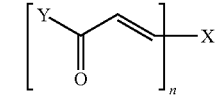

<Formula 1c>

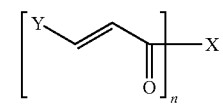

<Formula 1d>

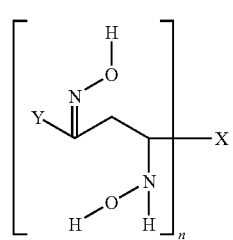

<Formula 1e>

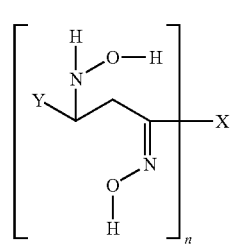

<Formula 1f>

In the production method,
definitions of n, X, Y, R1, R2, and R3 are the same as definitions of Formula 1a and Formula 1b.

The base that is used in the step 1) is sodium hydroxide or a sodium acetic acid, and may be used while being diluted in water in an appropriate amount. At this time, since the other compound is not dissolved in water, an alcohol solvent such as methanol, ethanol, isopropanol and the like may be further used. In particular, in consideration of the affinity to water, the exothermic property in the reaction and the toxicity, and the solubility, methanol is most preferable.

In the reaction of the step 2), $NH_2OH \cdot HCl$ and the sodium salt of the carboxylic acid may be used while being diluted in water in an appropriate amount. At this time, since the other compound is not dissolved in water, an alcohol solvent such as methanol, ethanol, isopropanol and the like may be further used. In particular, in consideration of the affinity to water, the exothermic property in the reaction and the toxicity, and the solubility, ethanol is most preferable.

In the reaction of the step 3), it is preferable that as the base, amine that is capable of removing toxious HCl generated in the reaction in a salt form is used, but it is not particularly limited thereto. At this time, as the used solvent, in the case of when it is not alcohol, it is not particularly limited thereto, but the solvent that has the good solubility in respects to the reactants and the products and is easily removed by a vacuum is preferable. As specific examples of this solvent, there are dichloromethane, chloroform, tetrahydrofurane, diethyl ether, ethyl acetate and the like.

Mode for the Invention

A better understanding of the present invention will be described in light of the following Examples which are set forth to illustrate, but are not to be construed to limit the present invention.

EXAMPLE

Example 1

1.2 mL of the 40% sodium hydroxide aqueous solution was mixed with the solution in which 2 g (14.9 mmol) of terephthalic aldehyde and 3.6 g (29.8 mmol) of acetophenone were dissolved in 50 mL of methanol at 0° C. After they were sufficiently mixed with each other at normal temperature for 5 hours or more, the produced white precipitate was filtered by using the filtering paper, and washed by using methanol. At this time, about 4.5 g of the precipitate was obtained, and the yield corresponded to 90%. The white precipitate was dissolved in $CDCl_3$, and analyzed by using the 500 MHz $^1H$ NMR, and the results are the same as the following description.

8.19-8.17 ppm (4H, d, ArH), 8.06-8.03 ppm (2H, d, —COCH=), 7.99 ppm (4H, s, ArH), 7.79-7.76 ppm (2H, d, =CH—), 7.70-7.66 ppm (2H, m, ArH), 7.60-7.57 ppm (4H, t, ArH).

The analysis results of the $^1H$ NMR are the same as the following Formula 2.

<Formula 2>

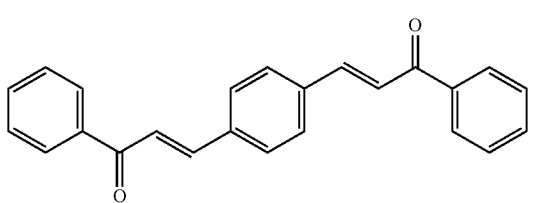

15 mL of the aqueous solution that comprised 4.9 g (70.9 mmol) of hydroxylamine hydrochloride (NH$_2$OH.HCl) and 5.8 g (70.9 mmol) of sodium acetate was added to 60 mL of the ethanol solution that comprised 3 g (8.8 mmol) of the white precipitate of Formula 2. After it was agitated for 1 hour by using the reflux device, the solution was cooled and poured to distilled water. After the white precipitate that was obtained by using this process was washed with distilled water, it was sufficiently dried at 40° C. for 5 hours or more. The amount of the obtained white precipitate was 2.2 g and the yield corresponded to about 58%.

The white precipitate was dissolved in DMSO d6 and analyzed by using the 500 MHz $^1$H NMR, and the results are the same as the following description.

11.25 ppm (2H, s, —NOH), 7.54-7.52 ppm (4H, m, ArH), 7.48-7.44 ppm (2H, m, ArH), 7.33-7.32 ppm (4H, m, ArH), 7.31 ppm (2H, s, —NOH), 7.17 ppm (4H, s, ArH), 5.85 ppm (2H, s, —NH), 4.16-4.13 ppm (2H, t, —NCH—), 3.14-3.09 ppm (2H, m, —NCH—HCH—), 2.99-2.95 ppm (2H, m, —NCH—HCH—).

The analysis results of the $^1$H NMR are the same as the following Formula 3.

<Formula 3>

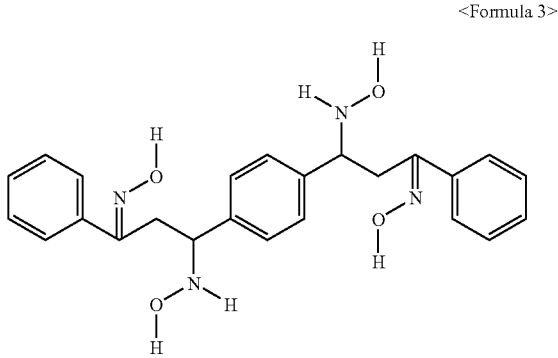

The solution in which 2.2 g (50 mmol) of the compound of the Formula 3 was dissolved in 30 mL of methylene chloride was maintained at 10° C., and 3.2 g (33.4 mmol) of triethyl amine and 2.6 g (33.4 mmol) of acetyl chloride were sequentially slowly added thereto. After they were agitated at normal temperature for 3 hours and further reacted, they were washed by using distilled water and brine, and dried by using sodium sulfuroxide (Na$_2$SO$_4$). The solvent was completely removed by using the vacuum. The residual material was subjected to the separation column to be purified by using the solution in which carbon dichloride and methanol were mixed with each other at a ratio of 95:5 as the eluant. 1.3 g of the product was obtained, and the yield corresponded to about 38%.

The produce that was obtained by the above process was dissolved in DMSO d6, and was analyzed by using the 500 MHz $^1$H NMR, and the results are the same as the following description.

7.66-7.63 ppm (4H, m, ArH), 7.51-7.49 ppm (2H, d, ArH), 7.47-7.44 ppm (4H, m, ArH), 7.29 ppm (4H, s, ArH), 5.65 ppm (2H, s, —NCH—), 3.76 ppm (2H, s, —NCH—HCH—), 3.44-3.41 ppm (2H, m, —NCH—HCH—), 2.22-2.21 ppm (6H, d, 2 —COCH$_3$), 2.08 ppm (6H, s, 2 —COCH$_3$), 1.68 ppm (6H, s, 2 —COCH$_3$).

The analysis results of the $^1$H NMR are the same as the following Formula 4.

<Formula 4>

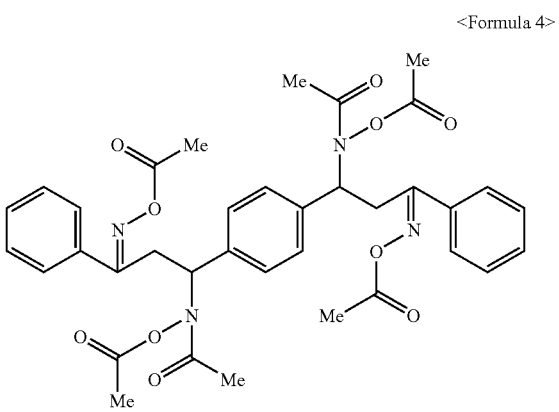

After the material of the Formula 4 was dissolved in acetonitrile in the concentration of 10$^{-5}$ M, the measured ultraviolet rays spectrum is the same as FIG. 1.

Example 2

0.6 mL of the 40% sodium hydroxide aqueous solution was mixed with the solution in which 1.0 g (6.1 mmol) of 1,4-diacetylbenzene and 1.8 g (12.3 mmol) of 4-methylthio-benzaldehyde were dissolved in 30 mL of isopropyl alcohol at 0° C. After they were sufficiently agitated at normal temperature for 5 hours or more and reacted with each other, the produced precipitate was washed by using distilled water and isopropyl alcohol. 2.6 g of the precipitate was obtained, and the yield corresponded to 100%.

The precipitate that was obtained by the above process was dissolved in CDCl$_3$, and was analyzed by using the 500 MHz $^1$H NMR, and the results are the same as the following description.

8.10 ppm (4H, s, ArH), 7.81-7.78 ppm (2H, d, —COCH=), 7.58-7.57 ppm (4H, d, ArH), 7.50-7.47 ppm (2H, d, =CH—), 7.28-7.26 ppm (4H, d, ArH), 2.53 ppm (6H, s, 2 SCH$_3$).

The analysis results of the $^1$H NMR are the same as the following Formula 5.

<Formula 5>

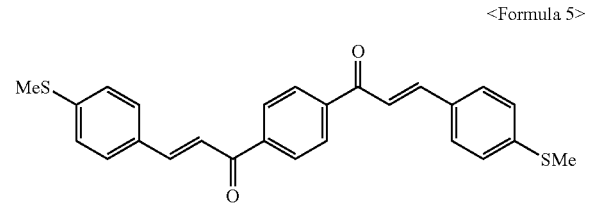

The solution in which 2.0 g (4.6 mmol) of the compound of Formula 5 was diluted in 100 mL of ethanol was added to the solution in which 2.6 g (37.1 mmol) of hydroxylamine hydrochloride (NH$_2$OH.HCl) and 3.0 g (37.1 mmol) of sodium acetate were mixed with 10 mL of distilled water. After they were agitated by using the reflux device for 2 hours and reacted with each other, the solution was cooled and poured to the distilled water. After the precipitate was filtered and washed by using the distilled water, it was dried at 40° C. 2.3 g of the solid material was obtained, and the yield corresponded to 96%.

The precipitate that was obtained by the above process was dissolved in DMSO d6, and was analyzed by using the 500 MHz $^1$H NMR, and the results are the same as the following description.

11.21 ppm (2H, s, —NOH), 7.49-7.48 ppm (4H, d, ArH), 7.27 ppm (2H, s, —NOH), 7.19-7.17 ppm (4H, d, ArH), 7.13-7.11 ppm (4H, dd, ArH), 5.92 ppm (2H, s, —NH), 4.10-4.07 ppm (2H, t, —NCH—), 3.11-3.02 ppm (4H, m, —NCH—HCH—), 2.41 ppm (6H, s, 2 SCH$_3$).

The analysis results of the $^1$H NMR are the same as the following Formula 6.

<Formula 6>

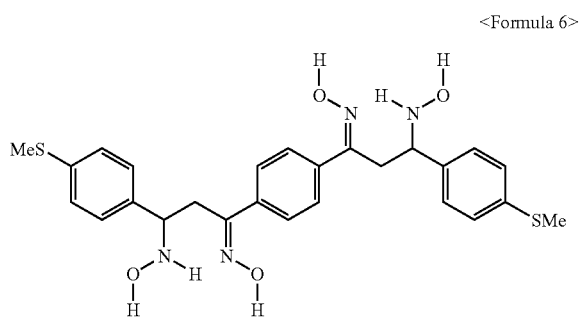

The solution in which 2 g (3.7 mmol) of the compound of the Formula 6 was dissolved in 30 mL of carbon dichloride was maintained at 10° C., and 2.5 g (25.0 mmol) of triethyl amine and 1.9 g (25.0 mmol) of acetyl chloride were sequentially slowly added thereto. After they were agitated at normal temperature and reacted for 3 hours, they were washed by using distilled water and brine, and dried by using sodium sulfuroxide (Na$_2$SO$_4$). The solvent was removed by using the vacuum, and the obtained material was subjected to the separation column to be purified by using the solution in which carbon dichloride and methanol were mixed with each other at a ratio of 95:5 as the eluant. 1.5 g of the product was obtained, and the yield corresponded to about 53%.

The produce that was obtained by the above process was dissolved in CDCl$_3$, and was analyzed by using the 500 MHz $^1$H NMR, and the results are the same as the following description.

7.65-7.64 ppm (4H, d, ArH), 7.17-7.15 ppm (4H, d, ArH), 7.13-7.12 ppm (4H, d, ArH), 5.76 ppm (2H, s, —NCH—), 3.66-3.61 ppm (2H, m, —NCH—HCH—), 3.59-3.53 ppm (2H, m, —NCH—HCH—), 2.45-2.44 ppm (6H, d, 2 —COCH$_3$), 2.27-2.26 ppm (6H, d, 2 —COCH$_3$), 2.04 ppm (6H, s, 2 —COCH$_3$), 1.85-1.83 ppm (6H, d, 2 SCH$_3$).

The analysis results of the $^1$H NMR are the same as the following Formula 7.

<Formula 7>

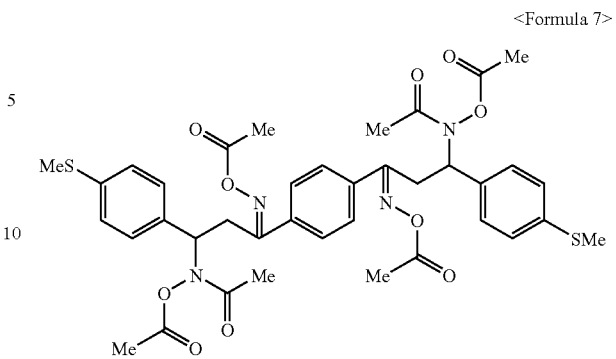

After the material of the Formula 7 was dissolved in chloroform in the concentration of $10^{-5}$ M, the measured ultraviolet rays spectrum was the same as FIG. 2.

Example 3

The solution in which 2.0 g (10.2 mmol) of N-ethylcarbazole was dissolved in 50 mL of carbon dichloride was maintained at 0° C., and 3.7 g (22.5 mmol) of cinnamoyl chloride was slowly mixed therewith. 3.0 g (22.5 mmol) of the anhydride powder of aluminum chloride was mixed therewith several times at 0° C. They were agitated at 0° C. for 2 hours and reacted with each other, the temperature was increased to normal temperature, and they were sufficiently reacted with each other for 5 hours or more, and poured to the distilled water that was cooled by the ice. The organic solution layer was washed by using the sodium hydrocarbonate saturated aqueous solution and brine and then dried by using sodium sulfate. The solvent was removed by using the vacuum. The material that was obtained by using the above process was crystallized by using ethanol to obtain 3.7 g of the solid material (yield about 80%).

The material that was obtained by the above process was dissolved in CDCl$_3$, and was analyzed by using the 500 MHz $^1$H NMR, and the results are the same as the following description.

8.89 ppm (2H, s, ArH), 8.27-8.25 ppm (2H, d, ArH), 7.91-7.88 ppm (2H, d, —COCH=), 7.78-7.75 ppm (2H, d, =CH—), 7.73-7.71 ppm (4H, d, ArH), 7.49-7.47 ppm (2H, d, ArH), 7.46-7.42 ppm (6H, m, ArH), 4.43-4.38 ppm (2H, q, —CH2—CH3), 1.50-1.47 ppm (3H, t, —CH2—CH3).

The analysis results of the $^1$H NMR are the same as the following Formula 8.

<Formula 8>

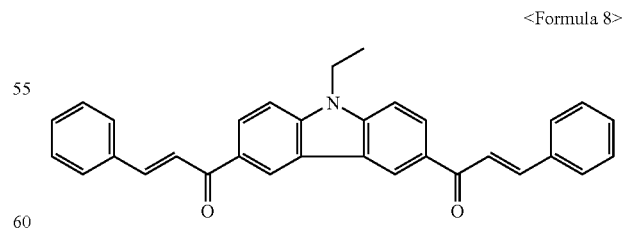

The 10 mL of the distilled water in which 4.2 g (61.4 mmol) of hydroxylamine hydrochloride and 5.0 g (61.4 mmol) of sodium acetate were dissolved was added to the solution in which 3.5 g (7.6 mmol) of Formula 8 was dissolved in 60 mL of ethanol. The solution was agitated under the reflux condition for 2 hours, cooled, and poured to the distilled water. The precipitate that was produced by using the above process was filtered, washed by using the distilled water, and sufficiently dried at 40° C. 4.1 g of the solid material was obtained and the yield was 100%.

The material that was obtained by the above process was dissolved in DMSO d6, and was analyzed by using the 500 MHz $^1$H NMR, and the results are the same as the following description.

11.02-11.01 ppm (2H, d, —NOH), 8.11-8.08 ppm (2H, d, —NOH), 7.69-7.66 ppm (2H, m, ArH), 7.53-7.51 ppm (2H, d, ArH), 7.34-7.28 ppm (6H, m, ArH), 7.27-7.23 ppm (4H, m, ArH), 7.17-7.15 ppm (2H, m, ArH), 6.00 ppm (2H, s, —NH), 4.43-4.41 ppm (2H, m, —NCH—), 4.29-4.25 ppm (2H, q, —CH$_2$—CH$_3$), 3.30-3.26 ppm (2H, m, —NCH—HCH—), 3.15-3.08 ppm (2H, m, —NCH—HCH—), 1.32-1.28 ppm (3H, t, —CH$_2$—CH$_3$).

The analysis results of the $^1$H NMR are the same as the following Formula 9.

<Formula 9>

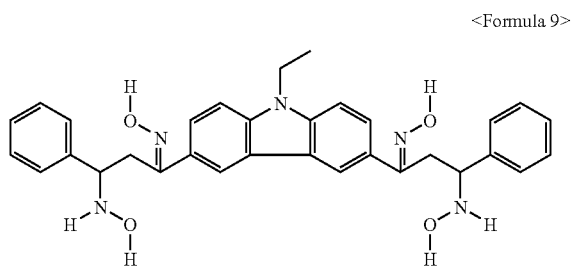

3.6 g (35.8 mmol) of triethyl amine and 2.8 g (35.8 mmol) of acetyl chloride were sequentially slowly mixed with the solution in which 3.0 g (5.4 mmol) of the compound of the Formula 9 was dissolved in 30 mL of carbon dichloride at 10° C. After they were agitated at normal temperature for 3 hours and further reacted, they were washed by using distilled water and brine, and dried by using sodium sulfuroxide. The solvent was completely removed by using the vacuum. The material that was obtained by using the above process was subjected to the separation column to be purified by using the solution in which carbon dichloride and methanol were mixed with each other at a ratio of 95:5 as the eluant. 3.3 g of the solid material was obtained, and the yield corresponded to about 76%.

The material that was obtained by the above process was dissolved in CDCl$_3$, and was analyzed by using the 500 MHz $^1$H NMR, and the results are the same as the following description.

8.42-8.39 ppm (2H, d, ArH), 7.87-7.85 ppm (2H, d, ArH), 7.42-7.40 ppm (2H, d, ArH), 7.35-7.27 ppm (10H, m, ArH), 5.92 ppm (2H, s, —NCH—), 4.41-4.35 ppm (2H, q, —CH$_2$—CH$_3$), 3.84-3.78 ppm (2H, m, —NCH—HCH—), 3.73-3.67 ppm (2H, m, —NCH—HCH—), 2.27 ppm (6H, s, —COCH$_3$), 2.03 ppm (6H, s, —COCH$_3$), 1.80-1.79 ppm (6H, d, —COCH$_3$), 1.46-1.43 ppm (3H, t, —CH$_2$—CH$_3$).

The analysis results of the $^1$H NMR are the same as the following Formula 10.

<Formula 10>

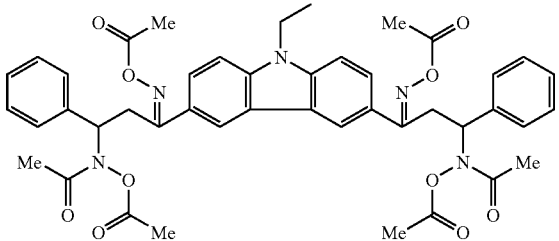

After the material of Formula 10 was dissolved in chloroform in the concentration of 10$^{-5}$ M, and the measured ultraviolet rays spectrum is the same as FIG. 3.

Example 4

The solution in which 2 g (10.2 mmol) of N-ethylcarbazole was dissolved in 50 mL of carbon dichloride was maintained at 0° C., 1.7 g (22.5 mmol) of acetyl chloride was dissolved, and 3 g (22.5 mmol) of the aluminum chloride anhydride powder was mixed therewith several times. They were agitated at 0° C., the reaction was performed for 2 hours, they were sufficiently reacted with each other at normal temperature for 5 hours or more, and the solution was poured to the distilled water that was cooled by the ice. The organic layer was washed by using the sodium hydrocarbonate saturated aqueous solution and brine, and dried by using sodium sulfate. The solvent was removed by using the vacuum, and the residual material was crystallized by using ethanol. 32.4 g of the solid material was obtained, and the yield corresponded to 85%.

The material that was obtained by the above process was dissolved in CDCl$_3$, and was analyzed by using the 500 MHz $^1$H NMR, and the results are the same as the following description.

8.74 ppm (2H, s, ArH), 8.16-8.14 ppm (2H, d, ArH), 7.43-7.41 ppm (2H, d, ArH), 4.40-4.36 ppm (2H, q, —CH$_2$—CH$_3$), 2.72 ppm (6H, s, —COCH$_3$, 1.47-1.44 ppm (3H, t, —CH$_2$—CH$_3$).

The analysis results of the $^1$H NMR are the same as the following Formula 11.

<Formula 11>

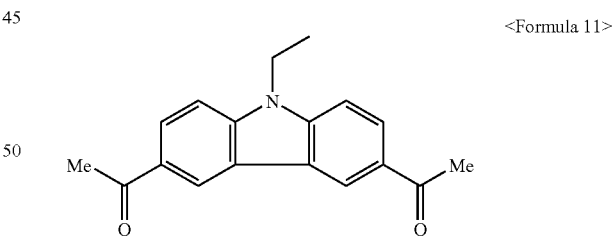

The solution in which 1 g (3.5 mmol) of the material of Formula 11 and 0.8 g (7.1 mmol) of the thiophene-2-carboxaldehyde were dissolved in isopropyl alcohol was maintained at 0° C., and 0.6 mL of the 40% sodium hydroxide aqueous solution was added thereto. They were sufficiently agitated at normal temperature for 5 hours or more, the obtained precipitate was filtered, and they were washed by using the distilled water and isopropyl alcohol. 1.4 g of the solid material was obtained, and the yield corresponded to about 88%.

The material that was obtained by the above process was dissolved in CDCl$_3$, and was analyzed by using the 500 MHz $^1$H NMR, and the results are the same as the following description.

8.89 ppm (2H, s, ArH), 8.26-8.24 ppm (2H, d, ArH), 8.05-8.02 ppm (2H, d, —COCH=), 7.59-7.56 ppm (2H, d, =CH—), 7.51-7.49 ppm (2H, d, ArH), 7.45-7.44 ppm (2H, d, Het), 7.41-7.40 ppm (2H, d, Het), 7.12-7.11 ppm (2H, t, Het), 4.46-4.41 ppm (2H, q, —CH$_2$—CH$_3$), 1.52-1.48 (3H, t, —CH$_2$—CH$_3$).

The analysis results of the $^1$H NMR are the same as the following Formula 12.

<Formula 12>

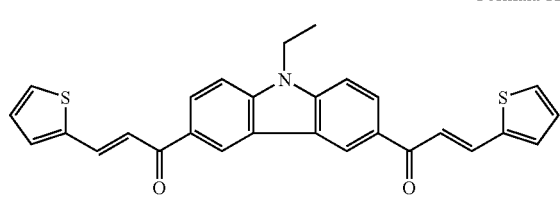

The solution in which 1.3 g (2.7 mmol) of the compound of Formula 12 was dissolved in 50 mL of ethanol was added to the solution in which 1.5 g (22.2 mmol) of Hydroxylamine hydrochloride and 1.8 g (22.2 mmol) of sodium acetate were dissolved in 10 mL of the distilled water. They were agitated for 2 hours, reacted, cooled, and poured to the distilled water. After the precipitate was filtered, the precipitate was washed by using the distilled water and sufficiently dried at 40° C. 1.4 g of the solid material was obtained, and the yield corresponded to 93%.

The material that was obtained by the above process was dissolved in DMSO d6, and was analyzed by using the 500 MHz $^1$H NMR, and the results are the same as the following description.

11.09 ppm (2H, s, —NOH), 8.14-8.13 ppm (2H, d, —NOH), 7.70-7.68 ppm (2H, d, ArH), 7.54-7.53 ppm (2H, d, ArH), 7.46 ppm (2H, s, ArH), 7.32-7.29 ppm (2H, t, Het), 6.92-6.90 ppm (2H, m, Het), 6.87-6.85 ppm (2H, t, Het), 5.91 ppm (2H, s, —NH), 4.56-4.54 ppm (2H, m, —NCH—), 4.46-4.39 ppm (2H, q, —CH$_2$—CH$_3$), 3.40-3.36 ppm (2H, m, —NCH—HCH—), 3.24-3.19 ppm (2H, m, —NCH—HCH—), 1.35-1.29 ppm (3H, t, —CH$_2$—CH$_3$).

The analysis results of the $^1$H NMR are the same as the following Formula 13.

<Formula 13>

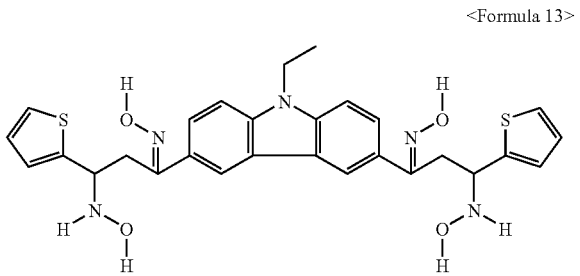

The solution in which 1.3 g (2.3 mmol) of the material of the Formula 13 was dissolved in 20 mL of carbon dichloride was maintained at 10° C., and 1.5 g (15.2 mmol) of triethyl amine and 1.2 g (15.2 mmol) of acetyl chloride were sequentially slowly mixed therewith. After the mixture that was obtained by using the above process were agitated at normal temperature for 3 hours and reacted, they were washed by using distilled water and brine, and dried by using sodium sulfate. The solvent was removed by using the vacuum. The residual material was subjected to the separation column to be purified by using the solution in which carbon dichloride and methanol were mixed with each other at a ratio of 95:5 as the eluant. 0.8 g of the solid material was obtained, and the yield corresponded to about 44%.

The material that was obtained by the above process was dissolved in CDCl$_3$, and was analyzed by using the 500 MHz $^1$H NMR, and the results are the same as the following description.

8.41-8.40 ppm (2H, d, ArH), 7.86-7.84 ppm (2H, d, ArH), 7.43-7.41 ppm (2H, d, ArH), 7.27-7.23 ppm (2H, t, Het), 7.00 ppm (2H, m, Het), 6.90-6.89 ppm (2H, t, Het), 6.24 ppm (2H, s, —NCH—), 4.40-4.35 (2H, q, —CH$_2$—CH$_3$), 3.80-3.66 (4H, m, —NCH—HCH—), 2.31 ppm (6H, s, —COCH$_3$), 2.14 ppm (6H, s, —COCH$_3$), 1.82 ppm (6H, d, —COCH$_3$), 1.46-1.43 ppm (3H, t, —CH$_2$—CH$_3$).

The analysis results of the $^1$H NMR are the same as the following Formula 14.

<Formula 14>

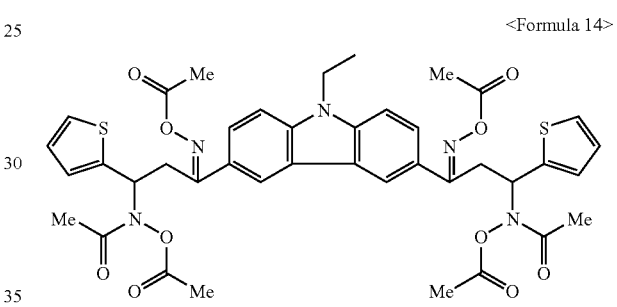

After the material of Formula 14 was dissolved in chloroform in the concentration of 10$^{-5}$ M, the measured ultraviolet rays spectrum was the same as FIG. 4.

Example 5

The solution in which 1.5 g (5.3 mmol) of 3,6-diacetyl-N-ethylcarbazole and 1.6 g (10.7 mmol) of 2-methylthio carboxaldehyde were dissolved in tert-butyl alcohol was maintained at 0° C., and 1 mL of the 40% sodium hydroxide aqueous solution was added thereto. They were sufficiently agitated at normal temperature for 5 hours or more, filtered, and washed by using the distilled water and tert-butyl alcohol. 2.9 g of the solid material was obtained, and the yield corresponded to 100%.

The material that was obtained by the above process was dissolved in CDCl$_3$, and was analyzed by using the 500 MHz $^1$H NMR, and the results are the same as the following description.

8.91 ppm (2H, s, ArH), 8.29-8.26 ppm (2H, d, ArH), 7.88-7.85 ppm (2H, d, —COCH=), 7.75-7.72 ppm (2H, d, =CH—), 7.65-7.64 ppm (4H, d, ArH), 7.52-7.50 ppm (2H, d, ArH), 7.30-7.29 ppm (2H, d, ArH), 4.47-4.42 ppm (2H, q, —CH$_2$—CH$_3$), 2.54 ppm (6H, s, —SCH$_3$), 1.52-1.48 ppm (3H, t, —CH$_2$—CH$_3$).

The analysis results of the $^1$H NMR are the same as the following Formula 15.

<Formula 15>

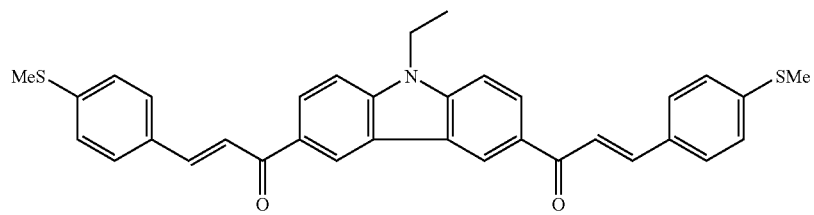

After 4.0 g (7.3 mmol) of the compound of Formula 15 was dissolved in 100 mL of ethanol, it was poured to the solution in which 4 g (58.4 mmol) of hydroxylamine hydrochloride and 4.8 g (58.4 mmol) of sodium acetate were dissolved in 10 mL thereof. Under the reflux conditions, they were agitated for 2 hours, reacted, cooled, and poured to the distilled water. After the precipitate was filtered, the precipitate was washed by using the distilled water and sufficiently dried at 40° C. 3.7 g of the solid material was obtained, and the yield corresponded to 79%.

The material that was obtained by the above process was dissolved in DMSO d6, and was analyzed by using the 500 MHz $^1$H NMR, and the results are the same as the following description.

10.98-10.97 ppm (2H, d, —NOH), 8.20-8.17 ppm (2H, d, —NOH), 7.71-7.68 ppm (2H, m, ArH), 7.55-7.53 ppm (2H, d, ArH), 7.28-7.27 ppm (2H, d, ArH), 7.26-7.23 ppm (4H, m, ArH), 7.13-7.12 ppm (4H, d, ArH), 5.99 ppm (2H, s, —NH), 4.45-4.41 ppm (2H, m, —NCH—), 4.23-4.19 ppm (2H, q, —CH$_2$—CH$_3$), 3.29-3.24 ppm (2H, m, —NCH—HCH—), 3.19-3.12 ppm (2H, m, —NCH—HCH—), 2.35-2.34 ppm (6H, d, —SCH$_3$), 1.33-1.30 (3H, t, —CH$_2$—CH$_3$).

The analysis results of the $^1$H NMR are the same as the following Formula 16.

amine and 2.8 g (35.8 mmol) of acetyl chloride were sequentially slowly mixed therewith. After they were agitated at normal temperature for 3 hours and reacted, they were washed by using distilled water and brine, and dried by using sodium sulfate. The solvent was removed by using the vacuum. The material that was obtained by using the above process was subjected to the separation column to be purified by using the solution in which carbon dichloride and methanol were mixed with each other at a ratio of 95:5 as the eluant. 3.5 g of the solid material was obtained, and the yield corresponded to about 73%.

The material that was obtained by the above process was dissolved in CDCl$_3$, and was analyzed by using the 500 MHz $^1$H NMR, and the results are the same as the following description.

8.44 ppm (2H, s, ArH), 7.86-7.84 ppm (2H, d, ArH), 7.43-7.41 ppm (2H, d, ArH), 7.25-7.22 ppm (4H, m, ArH), 7.14-7.11 ppm (4H, m, ArH), 5.86 ppm (2H, s, —NCH—), 4.40-4.36 ppm (2H, q, —CH2—CH3), 3.79-3.75 ppm (2H, m, —NCH—HCH—), 3.72-3.67 ppm (2H, m, —NCH—HCH—), 2.42-2.41 ppm (6H, d, —SCH3), 2.28 ppm (6H, s, —COCH3), 2.05 ppm (6H, s, —COCH3), 1.80 ppm (6H, d, —COCH3), 1.47-1.44 ppm (3H, t, —CH2—CH3).

<Formula 16>

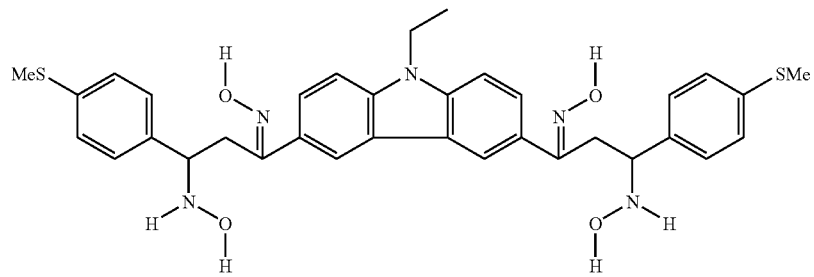

The solution in which 3.5 g (5.4 mmol) of the compound of the Formula 16 was dissolved in 30 mL of carbon dichloride was maintained at 10° C., and 3.6 g (35.8 mmol) of triethyl The analysis results of the $^1$H NMR are the same as the following Formula 17.

<Formula 17>

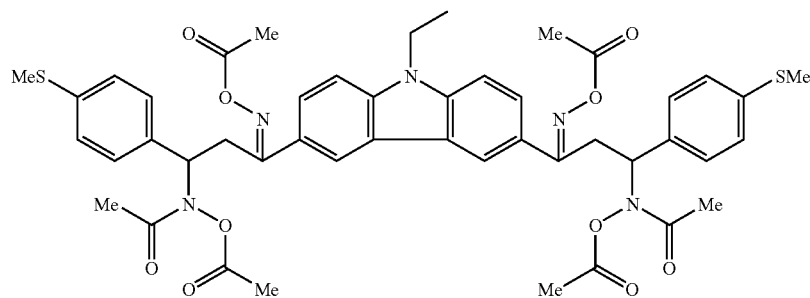

After the material of Formula 17 was dissolved in chloroform in the concentration of $10^{-5}$ M, the measured ultraviolet rays spectrum was the same as FIG. 5.

Comparative Example 1

For the comparison of the solubility of the compound that comprises oxime ester, in conjunction with Irgacure OXE-02 (Comparative Example 1) of Ciba Specialty Chemical, the solubilities of the compounds of Examples were measured in respects to the solvents that were frequently used, such as propylene glycol methyl ether acetate (PGMEA), dipropylene glycol methyl ether (DPM), 3-methoxybutyl acetate (MBA), ethyl-3-ethoxy propionate (EEP), and cyclohexanone (CH). The solubility was measured on the basis of how many grams of the photoinitiator were dissolved in 100 g of the solvent, and the results are described in the following Table 1.

TABLE 1

| Photo-initiator | PGMEA | DPM | 3-MBA | EEP | CH |
|---|---|---|---|---|---|
| Comparative Example 1 | 12 | 5 | 10 | 10 | 40 |
| Example 1 | 100 or more | 50 or more | 50 or more | 50 or more | 100 or more |
| Example 2 | 100 or more | 50 or more | 50 or more | 50 or more | 100 or more |
| Example 3 | 100 or more | 50 or more | 50 or more | 50 or more | 100 or more |
| Example 4 | 100 or more | 25 | 30 | 30 | 100 or more |
| Example 5 | 100 or more | 50 or more | 50 or more | 50 or more | 100 or more |

Comparative Example 2

For the comparison of the photosensitivities of the compounds that comprised oxime ester, in conjunction with Irgacure OXE-02 (Comparative Example 2) of Ciba Specialty Chemical, the the photosensitivities of the compounds of Examples were measured by using the FT-IR. After the photoinitiator and 2 moles of pentaerythritol triacrylate were dissolved in 10 g of cyclohexanone, it was spin coated on the glass substrate to form a thin film that had the thickness of 2 microns, and the thin film was heated at 100° C. for 2 min by using the hot plate to remove the solvent. The FT-IR of the thin film was measured, light of the maximum absorption wavelength of each sample was irradiated in the intensity of 30 mW/cm² for 10 min, and the consumption amounts of acrylate were compared to each other. The high pressure mercury lamp was used as the light source, and the wavelength was tested by the optical filter (the products that were manufactured by Mellis-Griot, Co., Ltd). The results are described in the following Table 2.

TABLE 2

| Photoinitiator | Consumption amount of acrylate |
|---|---|
| Comparative Example 2 | 5.4 moles |
| Example 1 | 5.2 moles |
| Example 2 | 6.2 moles |
| Example 3 | 6.2 moles |
| Example 4 | 5.8 moles |
| Example 5 | 5.6 moles |

The invention claimed is:

1. A dendritic photoactive compound is represented by the following Formula 1a or Formula 1b:

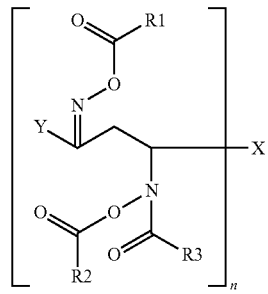

Formula 1a

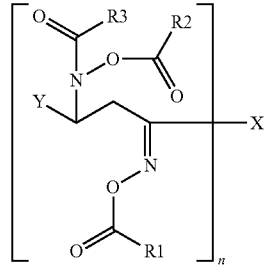

Formula 1b wherein n is 2,

X is a phenylene, biphenylene, bisphenylene, or naphthylene that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; a $C_5$~$C_{20}$ arylene group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; or a $C_4$~$C_{20}$ divalent heterocyclic group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group and comprises O, N or S; or X is

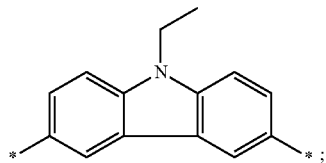

Y is selected from the group consisting of a $C_1$~$C_6$ alkyl group; a phenyl group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; a $C_5$~$C_{20}$ aryl group that is unsubstituted or substituted with one or more groups selected from the group consisting of halogen, CN, a $C_1$~$C_6$ group, a $C_1$~$C_6$ alkoxy group, a $C_1$~$C_6$ alkylthio group, and a morpholino group; and a $C_4$~$C_{20}$ heterocyclic group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group and comprises O, N or S, and R1, R2, and R3 are each independently selected from the group consisting of a $C_1$~$C_6$ alkyl group, nitrile group and phenyl group.

2. The dendritic photoactive compound according to claim 1, wherein the compound that is represented by Formula 1a or Formula 1b is any one selected from the fallowing Formula 4, Formula 7, Formula 10, Formula 14, and Formula 17:

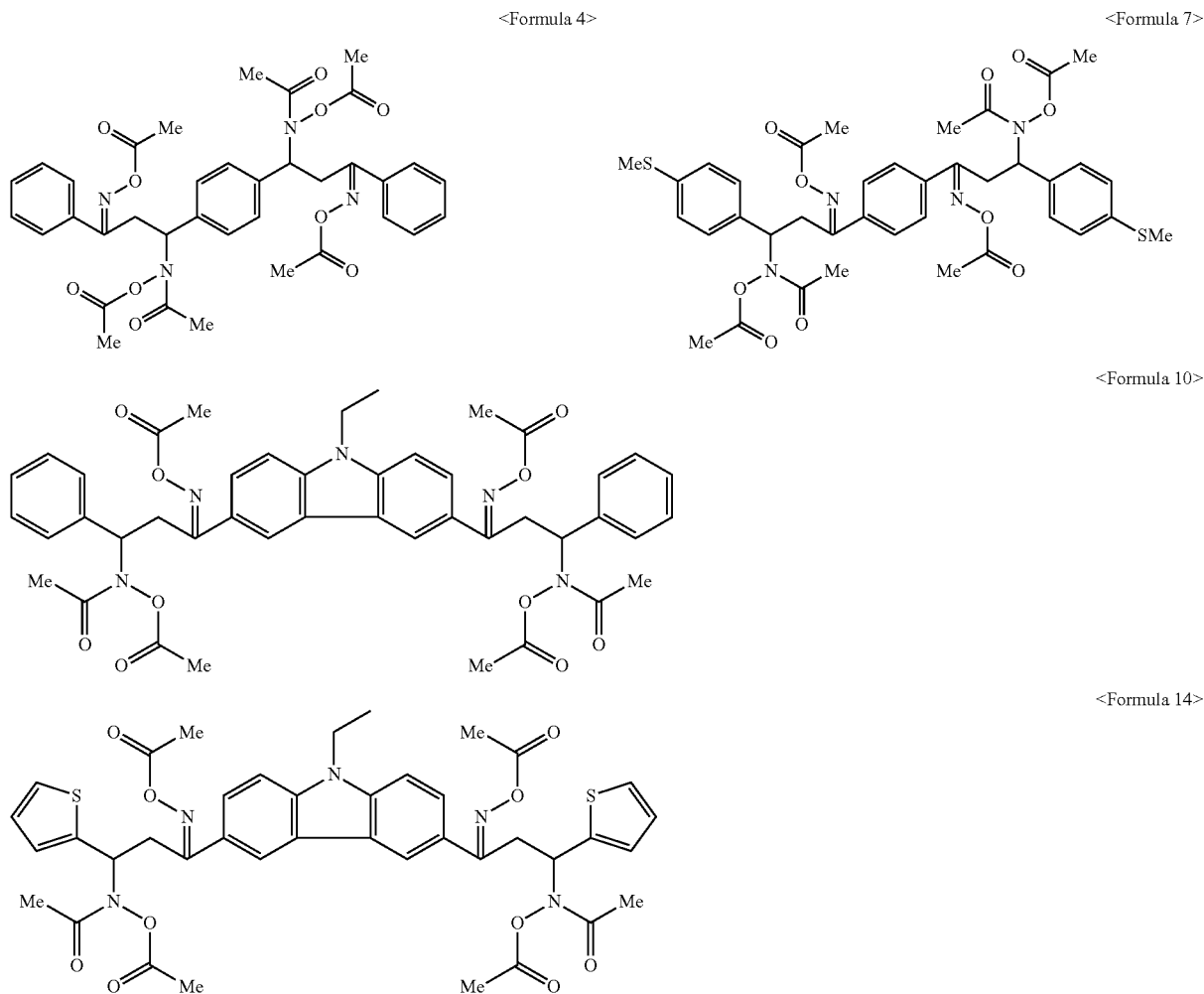

<Formula 17>

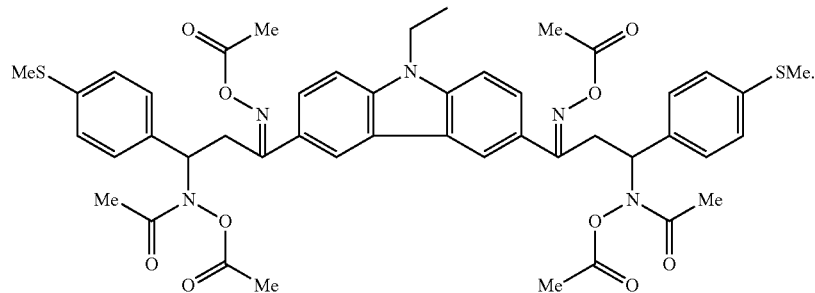

3. A method for producing the dendritic photoactive compound of claim 1, the method comprising the steps of:

1) reacting a ketone that is substituted with an aldehyde and a methyl under the presence of a base to produce a compound that is represented by the following Formula 1c or Formula 1d;
2) adding NH$_2$OH.HCl and a sodium salt of a carboxylic acid to the compound that is produced in the step 1) to produce a compound that is represented by the following Formula 1e or Formula 1f; and
3) adding R1—C(O)—Cl, R2—C(O)—Cl, R3—C(O)—Cl and the base to the compound that is produced in the step 2) to produce the dendritic photoactive compound that is represented by the following Formula 1a or Formula 1b:

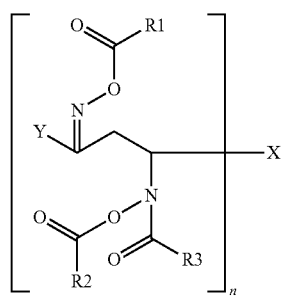

Formula 1a

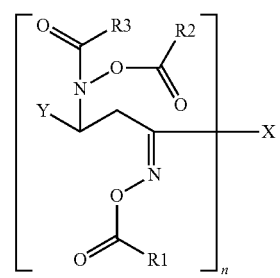

Formula 1b

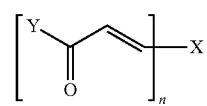

Formula 1c

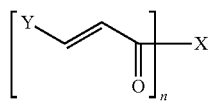

Formula 1d

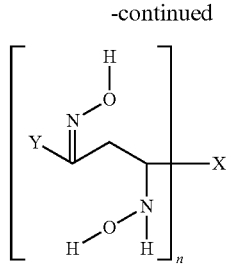

Formula 1e

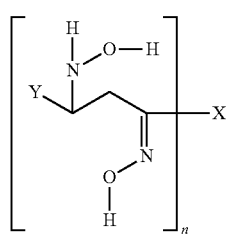

Formula 1f wherein
n is 2,
X is a phenylene, biphenylene, bisphenylene, or naphthylene that is unsubstituted or substituted with one or more groups selected from the group consisting of halogen, CN, a C$_1$~C$_6$ alkyl group, a C$_1$~C$_6$ alkoxy group, a C$_1$~C$_6$ alkylthio group, and a morpholino group; a C$_5$~C$_{20}$ arylene group that is unsubstituted or substituted with one or more groups selected from the group consisting of halogen, CN, a C$_1$~C$_6$ alkyl group, a C$_1$~C$_6$ alkoxy group, a C$_1$~C$_6$ alkylthio group, and a morpholino group; or a C$_4$~C$_{20}$ divalent heterocyclic group that is unsubstituted or substituted with one or more groups selected from the group consisting of halogen, CN, a C$_1$~C$_6$ alkyl group, a C$_1$~C$_6$ alkoxy group, a C$_1$~C$_6$ alkylthio group, and a morpholino group and comprises O, N or S; or X is

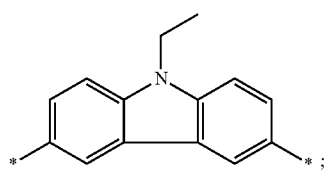

Y is selected from the group consisting of a C$_1$~C$_6$ alkyl group; a phenyl group that is unsubstituted or substituted with one or more groups selected from the group consisting of halogen, CN, a C$_1$~C$_6$ alkyl group, a C$_1$~C$_6$ alkoxy group, a $C_1$~$C_6$ alkylthio group, and a morpholino group; a $C_5$~$C_{20}$ aryl group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group; and a $C_4$~$C_{20}$ heterocyclic group that is unsubstituted or substituted with one or more groups selected from the group consisting of halogen, CN, a $C_1$~$C_6$ alkyl group, a $C_1$~$C_6$ alkoxy group, a $C_1$~$C_6$ alkylthio group, and a morpholino group and comprises O, N or S, and R1, R2, and R3 are each independently selected from the group consisting of a $C_1$~$C_6$ alkyl group, nitrile group and phenyl group.

4. The method according to claim 3, wherein the base is sodium hydroxide or a sodium acetic acid in the step 1).

5. The method according to claim 3, wherein the base is used while being diluted in water in the step 1).

6. The method according to claim 5, wherein any one that is selected from methanol, ethanol, and isopropanol is further used as the solvent in the step 1).

7. The method according to claim 3, wherein $NH_2OH \cdot HCl$ and a sodium salt of a carboxylic acid are used while being diluted in water in the step 2).

8. The method according to claim 7, wherein any one that is selected from methanol, ethanol, and isopropanol is further used as the solvent in the step 2).

9. The method according to claim 3, wherein the base is an amine in the step 3).

10. The method according to claim 9, wherein any one that is selected from dichloromethane, chloroform, tetrahydrofurane, diethyl ether, and ethyl acetate is further used as the solvent in the step 3).

* * * * *